United States Patent

Welbourn et al.

[11] Patent Number: 6,014,208
[45] Date of Patent: Jan. 11, 2000

[54] EXAMINING A DIAMOND

[75] Inventors: Christopher Mark Welbourn, Waltham St. Lawrence; Martin Phillip Smith, Wargrave; James Gordon Charters Smith, High Wycombe; Paul Martyn Spear, Maidenhead; Philip Maurice Martineau, Littlewick Green; Martin Cooper, Marlow, all of United Kingdom

[73] Assignee: Gersan Establishment, Liechtenstein

[21] Appl. No.: 09/000,098

[22] PCT Filed: Jul. 22, 1996

[86] PCT No.: PCT/US96/01751

§ 371 Date: Mar. 27, 1998

§ 102(e) Date: Mar. 27, 1998

[87] PCT Pub. No.: WO97/04302

PCT Pub. Date: Feb. 6, 1997

[30]    Foreign Application Priority Data

Jul. 24, 1995 [GB] United Kingdom .................... 9515143

[51] Int. Cl.[7] ................................................... G01N 21/00
[52] U.S. Cl. ...................... 356/237.1; 356/239.1; 356/239.7
[58] Field of Search ............................ 356/30, 237, 432, 356/301, 317, 318, 417; 250/458.1, 459.1, 461.1, 461.2

[56]    References Cited

U.S. PATENT DOCUMENTS

| | | | |
|---|---|---|---|
| 4,284,897 | 8/1981 | Sawamura et al. | 250/461 B |
| 4,799,786 | 1/1989 | Gerrard | 356/30 |
| 5,118,181 | 6/1992 | Yifrach et al. | 356/30 |
| 5,406,367 | 4/1995 | Sopori | 356/30 |
| 5,536,943 | 7/1996 | Smith et al. | 250/372 |

FOREIGN PATENT DOCUMENTS

| | | |
|---|---|---|
| 82201315 | 6/1991 | . |
| 0 425 426 | 5/1991 | European Pat. Off. . |
| 2 244 329 | 11/1991 | United Kingdom . |
| 2275788 | 7/1994 | United Kingdom . |
| 2 275 788 | 9/1994 | United Kingdom . |
| 2 293 236 | 3/1996 | United Kingdom . |

*Primary Examiner*—Frank G. Font
*Assistant Examiner*—Michael P. Stafiro
*Attorney, Agent, or Firm*—Ceasari and McKenna, LLP

[57]    ABSTRACT

In order to test whether a diamond has had a layer of synthetic diamond deposited thereon, it is irradiated with high energy ultraviolet radiation to cause emission of luminescence, the luminescence intensity produced by different zones of the diamond being measured and compared. In one embodiment an integrating enclosure (15) is used and the diamond (13) is mounted on a rotatable mount (14).

36 Claims, 2 Drawing Sheets

EXAMINING A DIAMOND

BACKGROUND TO THE INVENTION

The present invention relates to a method of and apparatus for testing whether a natural diamond has had a layer of synthetic diamond deposited thereon. This is of particular importance in testing whether the diamond is wholly natural or whether any part of it comprises CVD diamond material and also in locating such material if present.

Synthetic diamond material may be deposited on an uncut or part processed natural diamond which is then worked, for example, into a round brilliant cut. Alternatively, the synthetic diamond material coating may be deposited onto a fully fashioned brilliant stone after working of the stone. The thickness of the synthetic diamond material layer may be very thin (it could be in the range from 5 microns to 10 microns) but the present invention may also be used to detect thicker layers.

The value of a diamond is in part dependent upon its weight. Accordingly, synthetic diamond material may be deposited onto natural gem diamonds, before or after cutting of the diamond, to increase the weight of the finished product.

However, the value of a diamond also resides in its qualities of authenticity and uniqueness and in the fact that it is an entirely natural (i.e. mined) product. Thus, a diamond that has not been enlarged by deposition of synthetic diamond material has a value over a diamond which has.

Over the years, a number of methods of synthesising diamond material have been developed. One of these methods is the chemical vapour deposition (CVD) technique, which is a low pressure technique involving deposition of synthetic diamond (referred to as CVD diamond material in this specification) onto a substrate from a gas. CVD is the most likely way in which synthetic diamond will be deposited on a diamond, although alternative techniques such as physical vapour deposition have been proposed. A diamond artificially enlarged by deposition of CVD or similar diamond material is referred to in this specification as a "CVD/natural diamond doublet".

CVD diamond material may be deposited on a non-diamond or diamond substrate. In the latter case, the CVD diamond material can replicate the structure of the diamond substrate (referred to as "homoepitaxial growth"). The CVD/natural diamond doublet produced can be identical in appearance, density and other common physical properties to an entirely natural stone and there may be a problem in identifying such a CVD/natural diamond doublet.

It is an object of the present invention to provide a method of and apparatus for testing whether a diamond has had a layer of synthetic diamond deposited thereon.

It is desired that the apparatus should be simple and may be put into operation by a person with relatively little training. The method and apparatus should be capable of being operated reliably and consistently by a practised jeweler who has no training in laboratory gemological analysis. The method and apparatus should be suitable for screening large numbers of stones, one at a time, and should be suitable for automation.

British patent application No 9404309.8 discloses a method of determining whether a diamond has had a layer of synthetic diamond deposited thereon in which the diamond is caused to luminesce with electrons or high energy ultraviolet radiation and the resulting pattern of luminescence is observed to detect zones of superficial synthetic diamond. Preferably, the whole diamond is irradiated and the pattern observed by eye through magnifying means or on a screen via a CCD camera.

The present invention provides a method of testing whether a diamond has had a layer of synthetic diamond deposited thereon, comprising observing a plurality of zones of the surface of the diamond, each zone being observed by irradiating the zone with high energy radiation to excite or stimulate emission of luminescence and assessing the intensity of the luminescence.

The present invention further provides an apparatus for testing whether a diamond has a layer of synthetic diamond deposited thereon, comprising a mounting means, a support for a diamond, movably mounted on the mounting means, means for irradiating a diamond supported in the support with high energy radiation to excite or stimulate emission of luminescence, and means for providing a signal dependent upon the intensity of luminescence produced when a diamond mounted on the support is irradiated. Means for driving the support with respect to the mounting means may be provided. The mounting means may be fixed with respect to the irradiating means.

The invention further provides an apparatus for testing whether a diamond has had a layer of synthetic diamond deposited thereon, comprising an integrating enclosure having a support for a diamond, means for irradiating a zone of a diamond mounted on the support, and means for giving a signal dependent upon the flux intensity of luminescence in the integrating enclosure, produced when a diamond in the integrating enclosure is irradiated. The support for the diamond may be movable with respect to the integrating enclosure and may be driven by drive means.

The inventors have discovered that seeking substantial differences in the luminescence of different zones of a diamond provides a particularly simple way to locate superficial layers of synthetic diamond material. No imaging or visual interpretation of a complex image by an operator, as in British patent application number 9404309.8, is required.

By luminescence is meant emitted radiation of a wavelength generally different to the irradiating radiation which causes it.

The luminescence intensity is preferably measured. Preferably, a signal dependent upon the intensity of luminescence from each zone is produced. Alternatively, the surface of the diamond may be scanned by a beam of irradiating radiation, any significant change in intensity of luminescence between one zone and the next being detected.

The diamond may be irradiated with ultraviolet radiation of suitable wavelength. Substantially all natural diamonds will luminesce if irradiated with radiation of wavelength less than 225 nm. It is accordingly preferable to use radiation of wavelength less than or approximately equal to 225 nm. The irradiating radiation may be substantially monochromatic or it may comprise a range or a set of wavelengths.

It is preferred that preponderantly only the surface region of the diamond is irradiated and caused to luminesce. This is because layers of synthetic diamond material may be relatively thin. If the irradiating radiation penetrates to a depth significantly greater than the thickness of the thin layer of synthetic diamond material, luminescence could be produced from underlying natural diamond material which would confuse or swamp out the luminescence from the synthetic diamond layer.

For this reason also, it is preferred that the diamond is irradiated with radiation of wavelength less than or approximately equal to 225 nm which is very strongly absorbed by all types of diamond. This is described in more detail in British patent application number 9404309.8.

The irradiating radiation may include radiation of wavelengths greater than 225 nm. Certain radiation bands of wavelength greater than 225 nm have different absorption characteristics in different types of diamond. Accordingly, such radiation could penetrate the layer theoretically being studied and cause luminescence in other areas of the diamond, which could confuse the results. Irradiating radiation of wavelength much greater than 225 nm may be confused with luminescing radiation. It is desirable that radiation of wavelength greater than 225 nm should be sufficiently low in intensity that luminescence from parts of the diamond apart from the zone of interest does not swamp out or reduce the contrast in observations of luminescence. Preferably at least 50% of the irradiation energy is at wavelengths less than 225 nm. Preferably, however, radiation of wavelengths greater than 225 nm should be substantially excluded by a suitable filter.

The diamond may alternatively be irradiated with a beam of electrons of suitable energy, but the apparatus would then be complicated.

The irradiating radiation must be of intensity sufficient to generate observable luminescence.

The irradiating radiation may be generated by any suitable means, for example a laser or other source. The irradiating radiation may be directed onto the gemstone by any suitable means. However, the attenuation of short wavelength ultraviolet radiation by normal optics is high and it is preferred to use optical equipment which has a high transmissivity at short ultraviolet wavelengths.

Radiation of wavelengths shorter than 180 nm is attenuated by normal UV optics and by oxygen in air and is effectively filtered out by the apparatus.

Preferably the radiation is focused onto the diamond. More preferably, the radiation is focused onto an area of the diamond which is smaller than the total presented surface area of the diamond. Most preferably the radiation is focused to a small spot and scanned over the surface of the diamond.

As set out in more detail in GB 9404309.8, radiation of wavelength less than 225 nm is absorbed predominantly in the surface region of the diamond. This is of assistance in the present invention in that luminescence observed when a given zone is irradiated will be predominantly dependent upon the composition of the surface of the zone irradiated.

The luminescence bands observed for various types of diamond (natural or synthetic) fall within a wide range of wavelengths, generally in the visible part of the spectrum. A signal dependent upon intensity of luminescence falling in a relatively narrow band or a relatively wide band may be given. In the latter case, it is preferable to provide a cut-off filter to exclude the irradiating radiation.

A synthetic diamond layer deposited upon a natural diamond may be identifiable if the luminescence thereof is a different colour to the luminescence of the natural part of the diamond or, more importantly, of a different intensity to the luminescence of the natural part of the diamond. Accordingly, when the plurality of zones are tested, significant differences (for example, the lower signal being of the order of 80%, preferably 50%, or less of the higher), in the intensity of luminescence produced by different zones of the diamond will suggest a CVD/natural diamond doublet. It is possible that differences in luminescence intensity do not originate in a layer of synthetic diamond. The present invention provides a useful guide. However, further testing may be beneficial.

It may be sufficient only to test a few zones (maybe only two) in order to detect a difference in the luminescence in different zones. Preferably, however, a large number of zones are observed.

The intensity of radiation may, in the method of the invention, be assessed by eye. In this case, means should be provided for exluding the hazardous ultraviolet radiation from the observer. If the luminescence is assessed by eye, it is not necessary to form an image of the zone irradiated if the irradiating radiation can be confined to the zone of interest and irradiation of other zones avoided. In that case, the luminescence, rather than the diamond will be observed in effect.

Preferably, the observed radiation comprises no irradiating radiation. A small amount of irradiating radiation may be tolerated in the observed radiation if it does not swamp out luminescence.

The luminesced radiation may be detected by any suitable means. For example, a beam splitter may be placed in the path of the irradiating radiation, being configured to direct luminesced radiation from the diamond to a detector. A filter for filtering out irradiating radiation may be provided for the detector.

Alternatively, the diamond may be placed in an integrating enclosure and a zone of the diamond irradiated with irradiating radiation. The integrating enclosure is provided with a detector for giving a signal dependent upon the intensity of luminescence in the integrating enclosure produced when the given zone is irradiated. The detector may include a filter for filtering out irradiating radiation.

Preferably, the integrating enclosure comprises an integrating sphere.

If an integrating enclosure is used, the zone of the diamond of interest must be irradiated and substantially no other zones.

The diamond may be irradiated using a beam of confined dimensions which may be produced, for example, by an aperture between the diamond and the radiation source.

Preferably, a single zone of the diamond is irradiated at any one time and a plurality of such zones are irradiated sequentially. However, a plurality of different zones of the diamond may be independently irradiated simultaneously and signals dependent upon the intensity of luminescence produced by each respective zone provided, in succession or simultaneously, the observations being subsequently compared.

The diamond may be placed with the zone of interest in contact with the aperture, to reduce the inclusion of light from other parts of the diamond. This arrangement is particularly suitable if a beam splitter is provided in the irradiation path for passing luminescence to a detector.

The confined beam may be of variable dimension or of fixed dimension. It may correspond in size to a facet of a worked diamond or to a part of a facet. Preferably, the confined beam is smaller than the maximum dimension of the diamond, or is adjustable in size to allow this. The aperture may be of size 1–15 mm across, preferably 5–10 mm. An iris aperture may be provided, adjustable in size for best results.

More preferably, the beam may be focussed to a small spot of size 1 micron–1 mm across, preferably 5–100 microns, and preferably scanned across the diamond.

Radiation emanating from the diamond may be passed to the detector through a filter. Preferably, the filter is a cut-off filter for filtering out the irradiating radiation. A further filter may be provided for passing selected luminescence bands. For example, a number of interchangeable filters could be used, each passing light of a different wavelength.

The beam is preferably scanned (ie moved continuously or semi continuously) over the surface of the diamond. Means for scanning the beam may be provided in the form of means for moving the beam with respect to the diamond. For example, the diamond may be rotated about an axis not coincident with the beam of radiation. Preferably, the axis is normal to the beam of radiation. Means may be provided for moving the diamond linearly with respect to the beam of radiation, for example in two directions normal to the beam of radiation.

Means may be provided for giving a signal if the intensity of radiation emitted by the diamond changes by an amount exceeding a predetermined value. This is particularly useful if the diamond is scanned continuously. It allows changes in surface composition to be readily identified. For example, the signal giving means may comprise means for giving a signal dependent upon intensity of radiation and signal generating means for giving a change signal if the intensity of radiation changes by a given amount. For example, the change signal may be given if the intensity of radiation measured changes by 5%, preferably by more than 10%, preferably by greater than 20%.

The signal generating means may comprise a timer so that a change signal is only given if the intensity of radiation changes by a predetermined amount within a predetermined period of time. Means may be provided for altering the period of time and/or the amount by which the signal must change before a signal is given.

In one embodiment of the invention, the diamond is placed in a rotatable mount and rotated continuously, whilst the intensity of luminescence is measured. A noisy or modulated DC signal (variations in intensity of luminescence being caused by naturally occurring slight local differences in diamond composition, and internal reflection and refraction) followed by a much broader pulse of higher or lower intensity will suggest a CVD/natural diamond doublet.

Preferably, the diamond is rotated a plurality of times in order to give a plurality of readings which may be combined statistically to give a statistically improved reading.

The invention is preferably used with fluorescence—that is, luminescence produced effectively instantaneously by a zone of a diamond when it is irradiated with an electron beam or high energy ultraviolet radiation.

The apparatus of the invention is preferably confined in a light-tight box. This is to exclude radiation from external sources from reaching the detector and to prevent the potentially harmful high energy ultraviolet radiation escaping and causing damage to skin and eyes.

The invention will be further described by way of example only with reference to the accompanying drawings, in which.

DETAILED DESCRIPTION OF THE DRAWINGS

Figure 1:
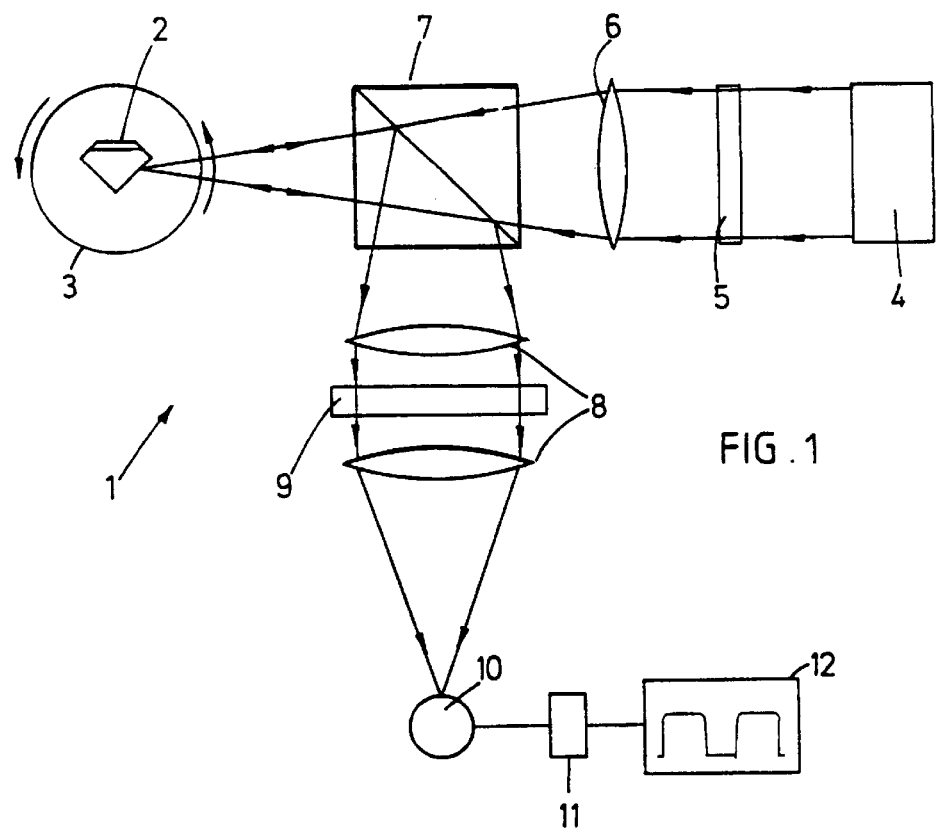
FIG. 1 is a schematic illustration of apparatus for carrying out the invention, according to a first embodiment.

In the apparatus generally designated as 1 in FIG. 1, a diamond 2 is mounted in or on a mounting 3 which is rotatable and which is transparent to shortwave ultraviolet light and to visible light. The diamond is irradiated with ultraviolet radiation of wavelength less than 225 nm. The radiation is generated by a source 4 (such as a Xenon flash lamp, deuterium lamp or ultraviolet laser). Irradiating radiation is filtered through a cut-off filter 5 which removes visible radiation, in order to improve the contrast of the luminescence observed. Radiation is focused onto a small zone of the diamond by a lens 6. The small zone of the diamond will be caused to luminesce, generating luminescence of intensity and colour dependent upon the local composition of the zone irradiated. Some of this luminescence passes back down the direction of irradiation to beam splitter 7 which passes luminescence through a lens system 8 having a filter 9 for removing radiation of wavelength less than 225 nm, the luminescence being focused onto a photomultiplier tube 10. The photomultiplier tube 10 is connected to a processor 11 and monitor 12 to display a signal dependent upon the luminescence produced.

In a preferred embodiment of the process of the invention, a plurality of zones of the diamond are irradiated by fixing the diamond with respect to rotatable mount 3 and rotating the mount (and the diamond) with respect to the rest of the apparatus so that the point of contact of the radiation moves over the surface of the diamond. The mount is also movable in a direction normal to the beam and to the axis of rotation so that the full height of the stone can be scanned by repeated rotations.

The diamond 2 shown in FIG. 1 is a CVD/diamond doublet, with a layer of CVD synthetic diamond material on the table of the diamond. The signal from the photomultiplier tube 10 displayed on monitor 12 as the diamond 2 is rotated will be a "noisy DC" signal as the irradiating radiation passes over the natural part of the stone, followed by a relatively broad dip to a lower (or higher) noisy DC signal as the focus of the irradiating radiation moves over the synthetic part of the stone, causing luminescence of a different intensity.

The "noise" will be due to small local variations in diamond composition, external and internal reflection and refraction etc.

The apparatus of FIG. 1 is not intended to detect the colour of the luminescence, though it may be modified to do so by providing a number of exchangeable coloured filters in front of the detector.

The optics used in FIG. 1 are UV transmitting optics such as those manufactured by Spindler & Hoyer.

Figure 2:
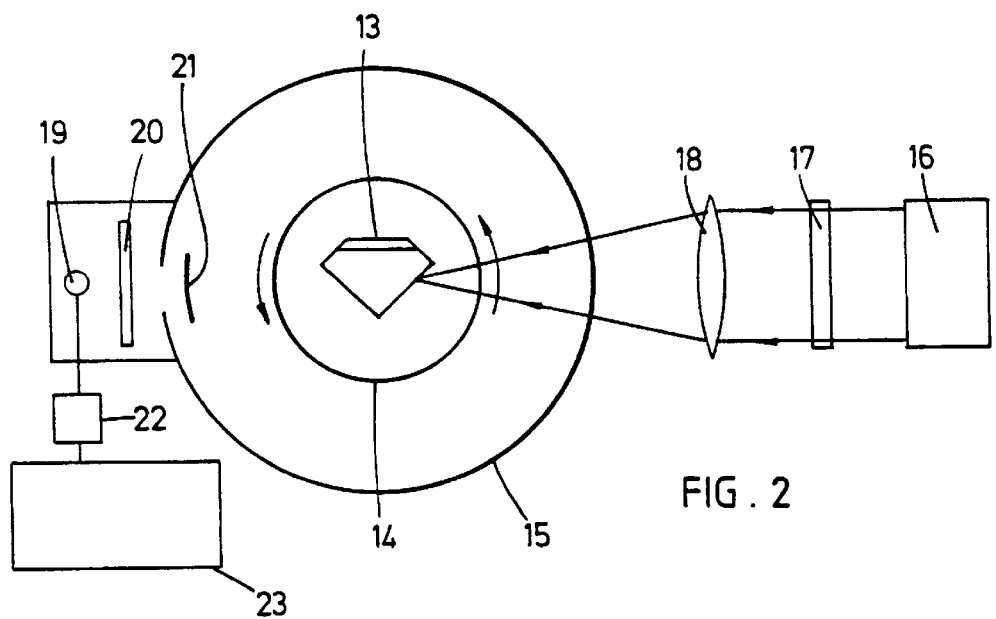
FIG. 2 is a schematic illustration of apparatus for carrying out the invention according to a second embodiment.

FIG. 2 shows a schematic apparatus for carrying out a method according to a second embodiment of the invention. In the apparatus, a diamond 13, which is a CVD/natural diamond doublet, is mounted on a rotatable mount similar to the mount 3 shown in FIG. 1. The mount and the diamond are placed inside an integrating sphere 15 which is lined with a material with good reflectance in the visible range. The diamond is irradiated using a UV source 16. Light from the source is passed through a filter 17 to remove light of wavelengths greater than 225 nm and is focused by a lens 18 onto the surface or near the surface of the diamond 13. The irradiating radiation is of wavelength less than 225 nm and therefore causes luminescence. Apparatus for detecting the luminous flux density of light at the luminescing wavelength (s) is provided in the form of a photomultiplier tube 19. A filter 20 is provided for filtering out the irradiating radiation and a baffle 21 is provided in the integrating sphere 15 to ensure that the radiation passing to the photomultiplier tube 19 is representative of the luminous flux density in the sphere. A processor 22 and monitor 23 is provided for showing the signal produced by the photomultiplier tube 19.

As the diamond 13 is a CVD/natural diamond doublet, the signal produced by the photomultiplier tube 19 when the mount 14 and diamond 13 are rotated is similar to that shown by the monitor in FIG. 1.

Figure 3:
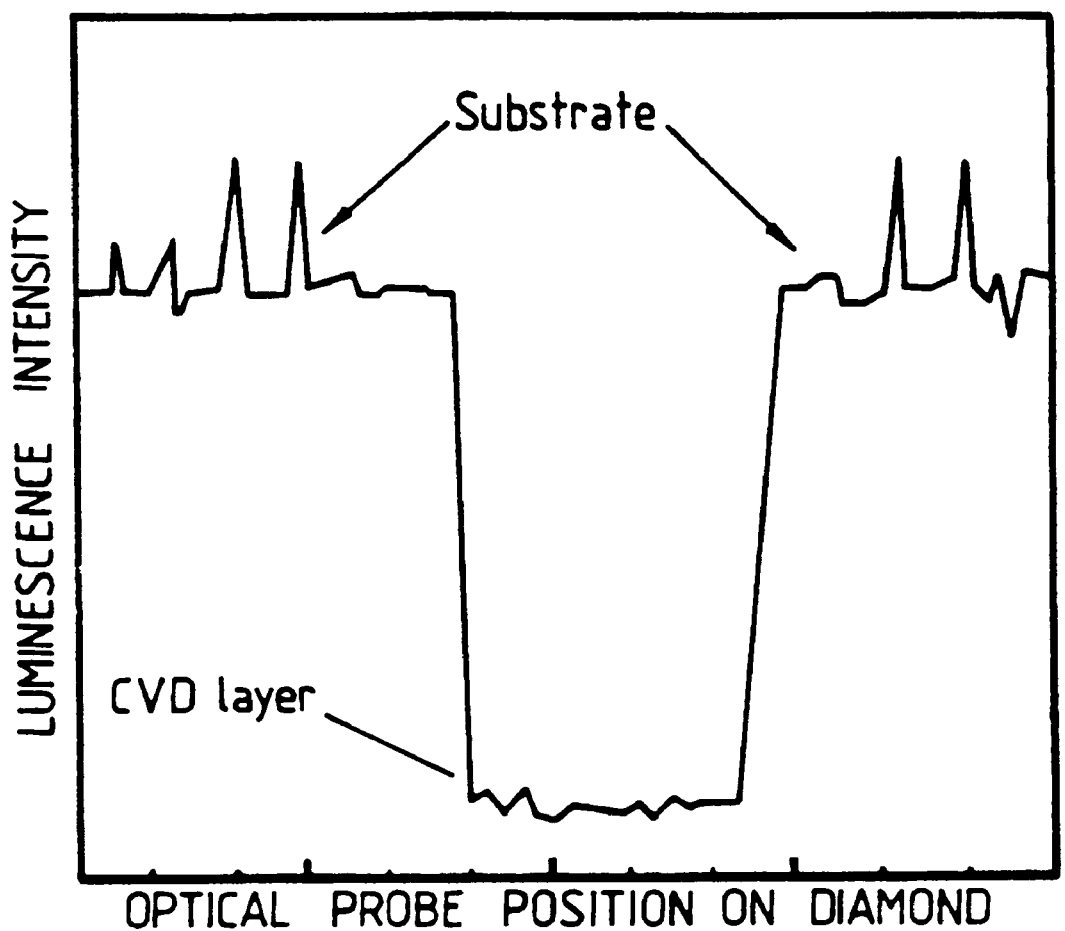
FIG. 3 shows a diagram of the signal output obtained.

FIG. 3 shows in more detail a signal produced by the photomultiplier tube 19 or 10 of FIG. 2 or 1 respectively. Fluctuations in the signal ("noise") due to natural variations in the diamond are distinct from changes in the signal due to layers of synthetic diamond in that fluctuations are lower in intensity and extend over smaller ranges of angles of rotation.

In an alternative embodiment, the processor 22 or 11 may be programmed to measure the rate of change of the signal received from the photomultiplier tube 19 or 10. The processor 11 or 22 may be connected to means for rotating the mount 3 or 14 respectively. The rate of change of the signal with respect to time or with respect to position of the mount 3 or 14 may be measured. The processing means 11 or 22 may be programmed to give a signal if the rate of change of the signal from the photomultiplier tube 10 or 19 exceeds a given value. A signal is then given, for example on monitor 12 or 23 to indicate that a "jump" in the emission of the diamond had been detected. Such a "jump" in emission can be correlated with the presence of a synthetic diamond layer.

The present invention has been described above purely by way of example, and modifications can be made within the spirit of the invention. The invention also consists in any individual features described or implicit herein or shown or implicit in the drawings or any combination of such features or any generalisation of any such features or combination.

We claim:

1. A method of testing whether a natural diamond has a layer of synthetic diamond deposited thereon, comprising irradiating a diamond with a small spot of high energy radiation to excite the emission of luminescence from the surface of the diamond, scanning in order to separately sense luminescence emitted by a plurality of different zones of the surface of the diamond, and determining whether there is a substantial change in the luminescence from one said zone to another to thereby determine whether there is a layer of synthetic diamond deposited on the natural diamond.

2. The method according to claim 1, wherein the diamond is irradiated with radiation preponderantly of a wavelength of less than 225 nm.

3. The method according to claim 1, wherein separate signals are provided dependant upon the luminescence emitted by the respective different zones.

4. The method according to claim 3, wherein the signals are dependant upon the intensity of lumninescence.

5. The method according to claim 3, wherein differences in the separate luminescence signals are automatically detected and an indicating signal is generated to automatically classify the diamond as having a layer of synthetic diamond deposited thereon if the differences exceed a predetermined value.

6. The method according to claim 5, wherein the indicating signal is generated if the intensity of luminescence from one zone to another chances by a predetermined amount within a predetermined period of time.

7. The method of any of claim 1 or 2, wherein whether there is a substantial change in the luminescence from one zone to another is determined by eye.

8. The method according to any of the preceding claim 1 or 2, wherein the scanning is effected by irradiating the diamond with a beam which is smaller than the diamond so that only a zone of the facing surface of the diamond is irradiated, and causing relative motion between the diamond and the beam so that the beam sequentially irradiate different zones of the diamond.

9. The method according to claim 8, wherein the beam is fixed and the diamond is moved.

10. The method of claim 8, herein the beam is fixed and the diamond is rotated.

11. The method of claim 8, wherein the diamond is supported within an intearating enclosure.

12. The method according to claim 1 or 2, wherein the diamond is irradiated with a beam providing a spot which is 5 to 100 microns across.

13. Apparatus for testing whether a natural diamond has a layer of synthetic diamond deposited thereon, comprising:
   a support for supporting a diamond;
   means for irradiating a diamond supported by the support with a small high spot of high energy radiation, to excite the emission of luminescence by the diamond;
   scanning means for providing separate signals dependant upon the luminescence emitted by a plurality of respective different zones of the surface of the diamond: and
   means for indicating on the basis of said signals whether the diamond has a layer of synthetic diamond deposited thereon.

14. The apparatus according to claim 13, wherein the irradiating means is for irradiating the diamond with radiation comprising radiation preponderantly of a wavelength of less than 225 nm.

15. The apparatus according to claim 13 or 14, wherein the signals are dependant upon the intensity of luminescence.

16. The apparatus according to any of claim 13 to 14, including means for automatically detecting differences in the separate luminescerce signals and for generating an indicating signal to automatically classify the diamond as having a layer of synthetic diamond deposited thereon if the differences exceed a predetermined value.

17. The apparatus according to claim 16, wherein the generating means generates the indicating signal if the intensity of luminescence from one zone to another changes by a predetermined amount Within a predetermined period of time.

18. The apparatus according to any of claim 13 or 14, wherein the irradiating means is for irradiating the diamond with a beam which is smaller than the diamond so that only a zone of the facing surface of the diamond is irradiated, and the scanning means causes relative motion between the diamond and the beam so that the beam sequentially irradiates different zones of the diamond.

19. The apparatus according to claim 18, wherein the irradiating means are for irradiating the diamond with a fixed beam and means are provided for moving the support.

20. The apparatus according to claim 18, wherein the irradiating means are for irradiating the diamond with a fixed beam and means are provided for rotating the support.

21. The apparatus of claim 8, wherein the diamond support is within an integrating enclosure.

22. The apparatus according to any of claim 13 or 14, wherein the irradiating means is for irradiating the diamond with a beam providing a spot on the diamond which is 5 to 100 microns across.

23. A method of testing whether a natural diamond has a layer of synthetic diamond deposited thereon, comprising irradiating generally along an irradiation axis a diamond with high energy radiation to excite the emission of luminescence from the surface of the diamond, rotating the diamond about an axis of rotation which is at a substantial angle to said irradiation axis in order to separately sense luminescence emitted by a plurality of different zones of the surface of the diamond, and determining whether there is a substantial change in the luminescence from one said zone to another to thereby determine whether there is a layer of synthetic diamond deposited on the natural diamond.

24. The method according to claim 23, wherein separate signals are provided dependent upon the luminescence emitted by respective said different zones, differences in the separate signals are automatically detected, and an indicating signal is generated to automatically classify the diamond as having a layer of synthetic diamond deposited thereon if the differences exceed a predetermined value.

25. The method according to claim 23, wherein the diamond is irradiated with a small spot of high energy radiation to excite the emission of luminescence from the surface of the diamond.

26. A method of testing whether a natural diamond has a layer of synthetic diamond deposited thereon, comprising supporting a diamond within an integrated enclosure, irradiating generally along an irradiation axis the diamond with high energy radiation to excite the emission of luminescence from the surface of the diamond, rotating the diamond about an axis of rotation which is at a substantial angle to said irradiation axis in order to separately sense luminescence at a luminescence wavelength emitted by a plurality of different zones of the surface of the diamond, and determining from any differences in the luminous flux density at the luminescing wavelength within the integrating enclosure whether there is a substantial change in the luminescence from one said zone to another, to thereby determine whether there is a layer of synthetic diamond deposited on the natural diamond.

27. The method according to claim 26, wherein separate signals are provided dependent upon the luminescence emitted by respective said different zones, differences in the separate signals are automatically detected, and an indicating signal is generated to automatically classify the diamond as having a layer of synthetic diamond deposited thereon if the differences exceed a predetermined value.

28. The method according to claim 26, wherein the diamond is irradiated with a small spot of high energy radiation to excite the emission of luminescence from the surface of the diamond.

29. Apparatus for testing whether a natural diamond has a layer of synthetic diamond deposited thereon, comprising a rotatable support for supporting a diamond for rotation about an axis of rotation, a high energy radiation emitter for irradiating generally along an irradiation axis a diamond supported by the support, to excite the emission of luminescence by the diamond, the irradiation axis making a substantial angle with the axis of rotation, wherein different zones of the surface of the diamond are irradiated, a detector for sensing the luminescence emitted by said different zones and providing separate signals dependent upon said luminescence, and a monitor for displaying said signals, thereby enabling an operator to determine whether the natural diamond has a layer of synthetic diamond deposited thereon.

30. The apparatus according to claim 29, and further comprising a beam splitter on said irradiation axis, for directing to said detector luminescence emitted by the surface of the diamond in the direction of the irradiating radiation.

31. Apparatus for testing whether a natural diamond has a layer of synthetic diamond deposited thereon, comprising a rotatable support for supporting a diamond for rotation about an axis of rotation, a high energy radiation emitter for irradiating generally along an irradiation axis a diamond supported by the support, to excite the emission of luminescence by the diamond, the irradiation axis making a substantial angle with the axis of rotation, wherein different zones of the surface of the diamond are irradiated, a detector for sensing the luminescence emitted by said different zones and providing separate signals dependent upon said luminescence, and a processor for indicating on the basis of said signals whether the natural diamond has a layer of synthetic diamond deposited thereon.

32. Apparatus for testing whether a natural diamond has a layer of synthetic diamond deposited thereon, comprising a rotating support for supporting a diamond for rotation about an axis of rotation, and a source of a fixed beam of high energy radiation for irradiating a diamond supported by the support with a spot of radiation which is substantially smaller than the maximum dimension of the diamond so that only a zone of the facing surface of the diamond is irradiated, to stimulate emission of luminescence, the fixed beam having an axis of irradiation which makes a substantial angle with the axis of rotation of the diamond wherein when a diamond mounted on the support is irradiated and is rotated, the intensity of luminescence of different said zones can be compared.

33. The apparatus according to claim 32, wherein separate signals are provided dependent upon the luminescence emitted by respective said different zones, differences in the separate signals are automatically detected, and an indicating signal is generated to automatically classify the diamond as having a layer of synthetic diamond deposited thereon if the differences exceed a predetermined value.

34. Apparatus for testing whether a natural diamond has had a layer of synthetic diamond deposited thereon, comprising an integrated enclosure, a support for a diamond within the integrating enclosure, the support being rotatable about an axis of rotation, a high energy radiation source for irradiating successive zones of the surface of the diamond along an irradiation axis which makes a substantial angle with the axis of rotation, while the diamond is rotated, to stimulate emission of luminescence;

a filter for filtering out the irradiating radiation, and a detector behind the filter for providing signals dependent upon the luminous flux density of luminescence within the integrating enclosure when the successive zones of the diamond are irradiated, wherein the presence or otherwise of a layer of synthetic diamond on the natural diamond can be assessed from variations in said signals.

35. The apparatus according to claim 34, wherein separate signals are provided dependent upon the luminescence emitted by respective said different zones, differences in the separate signals are automatically detected, and an indicating signal is generated to automatically classify the diamond as having a layer of synthetic diamond deposited thereon if the differences exceed a predetermined value.

36. The apparatus according to claim 34, wherein the diamond is irradiated with a small spot of high energy radiation to excite the emission of luminescence from the surface of the diamond.

* * * * *